United States Patent
Chan et al.

(10) Patent No.: US 6,275,726 B1
(45) Date of Patent: Aug. 14, 2001

(54) METHODS OF ENHANCED LIGHT TRANSMISSION THROUGH TURBID BIOLOGICAL MEDIA

(75) Inventors: Eric K. Chan, Maneville, OH (US); Jennifer K. Barton; Ashley J. Welch, both of Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/079,991

(22) Filed: May 15, 1998

Related U.S. Application Data (60) Provisional application No. 60/046,567, filed on May 15, 1997.

(51) Int. Cl.[7] .................................................. A61B 5/00
(52) U.S. Cl. ........................ 600/476; 600/310; 356/432
(58) Field of Search .................................. 600/473, 476, 600/310, 316; 604/19, 20, 289; 424/400, 427; 356/39, 432, 337

(56) References Cited

U.S. PATENT DOCUMENTS

| | | |
|---|---|---|
| 4,612,938 | 9/1986 | Dietrich et al. . |
| 4,810,875 * | 3/1989 | Wyatt .................................. 250/227 |
| 4,947,850 | 8/1990 | Vanderkooi et al. . |
| 5,200,430 * | 4/1993 | Federman ............................. 514/772 |
| 5,290,555 * | 3/1994 | Guthauser et al. ................... 424/401 |
| 5,336,175 * | 8/1994 | Mames . |
| 5,476,515 * | 12/1995 | Kelman et al. .......................... 623/6 |
| 5,565,215 * | 10/1996 | Gref et al. ............................ 424/501 |
| 5,647,364 | 7/1997 | Schneider et al. . |
| 5,674,470 | 10/1997 | Tweedle et al. . |
| 5,713,359 | 2/1998 | Dumoulin et al. . |
| 5,792,051 * | 8/1998 | Chance ................................. 600/310 |
| 5,823,951 * | 10/1998 | Messerschmidt ..................... 600/322 |
| 5,928,663 * | 7/1999 | Peyman ................................ 424/427 |

OTHER PUBLICATIONS

Albert et al., "Biological magnetic resonance imaging using laser–polarized [129]Xe," *Nature*, 370:199–201, 1994.

Bruulsema et al., "Optical properties of phantoms and tissue measured in vivo from 0.9–1.3 μm using spatially resolved diffuse reflectance," *SPIE* 2979:325–334, 1997.

Chance et al., "Effects of solutes on optical properties of biological materials: models, cells and tissues," *Analyt. Biochem.*, 227:351–362, 1995.

DeCoste et al., "Dye enhanced laser welding for skin closure," *Lasers in Surgery and Medicine*, 12:25–32, 1992.

Gregory, "Physical properties of glycerine," *In: Glycerine: A Key Cosmetic Ingredient*, Jungermann and Sonntag (Eds.), Marcel Cekker, Inc., NY, pp. 113–156, 1991.

Haglund et al., "Enhanced optical imaging of human gliomas and tumor margins," *Neurosurgery*, 38(2):308–317, 1996.

Hiramoto, "Refractive index of the protoplasm in sea urchin eggs," *Develop. Growth and Differentiation*, 1(2):141–148, 1979.

(List continued on next page.)

*Primary Examiner*—Marvin M. Lateef
*Assistant Examiner*—Shawna J. Shaw
(74) *Attorney, Agent, or Firm*—Fulbright & Jaworski, LLP (57) ABSTRACT

A new process to increase light transmission in biological tissue has been developed. The technique involves temporarily replacing tissue water with a fluid that has a refractive index closer to that of inter/intra cellular components. Subsequently, the amount of index mis-match between these components and the fluid environment is temporarily decreased. This lowers the amount of random reflection and refraction which also reduces light scattering. In addition, the infrared absorption is reduced when the fluid has a lower absorption coefficient than water. Furthermore, this process is reversible; thus creating a transient window to enhance light transmission for therapeutic and/or diagnostic applications.

24 Claims, 7 Drawing Sheets

OTHER PUBLICATIONS

Houlne et al., "Characterization of micro–endoscopie imaging systems for tissue spectroscopy," *SPIE*, 2678:464–474, 1996.

Huang et al., "Optical coherence tomography," *Science*, 1178–1181, 1991.

Izatt et al., "Micron–resolution biomedical imaging with optical coherence tomography," *Opt. Photon News*, 4:14–19, 1993.

Jungermann and Sonntag, "Glycerine: A key cosmetic ingredient," Dekker, NY, NY, 1991.

Kohl and Cope, "Influence of glucose concentration on light scattering in tissue–simulating phantoms," *Optics Letters*, 19(24):2170–2172, 1994.

Lawaczeck, "Water permeability through biological membranes by isotopic effects of fluorescence and light scattering," *J. Biophys.*, 45:491–494, 1984.

Maier et al., "Possible correlation between blood glucose concentration and the reduced scattering coefficient of tissues in the near infrared," *Optics Letters*, 19(24):2062–2064, 1994.

Prahl, "Optical property measurements using the inverse adding–doubling program," *A Computer Software for the PCs*, Mar. 1995.

Prahl, "The adding–double program," *In: Optical–thermal response of laser–irradiated tissue*, Welch and van Gemert (Eds), Plenum Press, NY, pp. 101–129, 1995.

Pickering et al., "Double–integrating sphere system for measuring the optical propertis of tissue," *Applied Optics*, 32(4):399–410, 1993.

Qu and Wilson, "The effect of physiological factors and other analytes on the determination of glucose concentration in vivo by optical absorption and scattering measurements," *SPIE*, 2679(236–242, 1996.

Sakatani et al., "Noninvasive optical imaging of the sub-arachnoid space and cerebrospinal fluid pathways based on near–infrared fluorescence," *J. Neurosurg.*, 87:738–745, 1997.

Schmitt et al., "Optical–coherence tomography of a dense tissue: Statistics of attenuation and backscattering," *Phys. Med. Biol.*, 39:1705–1720, 1994.

Tan, "Management and treatment of benign cutaneous vascular lesions," Lea & Febiger, Phil. PA, pp. 24–47, 53–67 and 83–99, 1992.

Tuchin et al., "Light propagation in tissues with controlled optical properties," IN: Proceedings of Photon Propagation in Tissues II, Benaron et al. (Eds.), *SPIE*, 2925:118–142, 1996.

Tuchin et al., "Light propagation in tissues with controlled optical properties," *J. Biomed. Optics.*, 2(4):401–417, 1997.

Vitkin et al., "Optical and thermal characterization of natural melanin," *Photochemistry and Photobiology*, 59:455–462, 1994.

Wang et al., "Group refractive index measurement of dry and hydrated type I collagen films using optical low–coherence reflectometry," *J. Biomed. Optics*, 1(2):212–216, 1996.

Wang et al., "Ballistic 2–D imaging through scattering walls using an ultrafast optical Kerr gate," *Reports*, 769–771, 1991.

Weast, *CRC Handbook of chemistry and physics*, CRC Press, Inc. Boca raton, FL. 1986.

Welch and Gemert, "Optical–thermal response of laser–irradiated tissue," Plenum Press, NY, NY, 1995.

* cited by examiner

METHODS OF ENHANCED LIGHT TRANSMISSION THROUGH TURBID BIOLOGICAL MEDIA

The present application claims priority to U.S. Provisional Patent Application Serial No. 60/046,567 filed May 15, 1997. The entire text of each of the above-referenced disclosure is specifically incorporated by reference herein without disclaimer.

BACKGROUND OF THE INVENTION

1. Field of the Invention

The present invention relates generally to the fields of biomedical engineering, medicine and imaging. More particularly, it concerns a new process to increase light transmission in biological media by using either index matching agents to reduce the amount of random reflection and refraction in tissue which, in turn, reduces light scattering or agents that reduce absorption and allow improved tissue imaging and delivery of light into tissues for diagnoses and treatment.

2. Description of Related Art

Many biological media or tissues, such as human skin, are optically turbid and highly light scattering because of the refractive index (n) variations among water and various inter/intra cellular components. The refractive index of water is 1.33 while many cellular components have higher refractive indices. For instance, melanin has a refractive index of 1.7 (Vitkin et al., 1994), nucleus has a refractive index of 1.36 Hiramoto, 1979) and dehydrated collagen has a refactive index of 1.53 (Wang et al., 1996). Reflection and refraction occur when light travels from a medium with one refractive index to another medium having a different index. Greater index mis-match generally increases the amount of light reflection and refraction As a result, light scatters randomly inside tissues mainly due to the index mis-match between cellular/subcellular water and the spatial distribution of various cellular components.

Imaging through tissue is always degraded by the strong optical scattering in biological tissue and any imaging technique must either discriminate in favor of the unscattered "ballistic" light signal (which is usually extremely weak) or must take account of the multiple scattering in some image reconstruction algorithm based on inverse scattering. Both approaches limit the visualization of the underlying tissue and in many cases turbid tissues cannot be sufficiently distinguished from each other. Thus many optical diagnostic and therapeutic techniques have limited capabilities.

Many current medical monitoring techniques require puncturing the skin to draw blood. For example, diabetics must measure the glucose concentration in blood samples which is extremely inconvenient and invasive, especially when one has to perform this task up to twenty times per day. A non-invasive blood glucose monitoring method is a goal of intensive research worldwide. One method uses the blood spectral absorbance to quantitatively determine glucose level, but the small glucose optical signature relative to noise and filtering associated with scattered light remains a serious constraint which has prevented the widespread adoption of this method for monitoring. Non-invasive devices are being developed to perform this absorbance measurement, but the signal to noise limitation must be reduced in order for these devices to be successful.

Development of noninvasive techniques appear to be further advanced for the visualization of the eye sclera, especially for the detection of cancers and cataracts. But these techniques have not been successfully applied to other tissues.

There are techniques which temporarily alter tissue optical properties such as stretching, coagulation and dehydration which cause the packing of cellular components to reduce reflection/refraction due to the cellular-water interface. Color dyes have been used to enhance local light absorption (DeCoste et al., 1992). Each of these techniques has limited applicability to living animals.

Radiation dispersing agents, irradiation and fluorescence have been used in combination to visualize and photosensitive tumor cells (U.S. Pat. No. 4,612,938). But this technique is designed to enhance visualization of tumor cells on the interior surface of hollow organ cavities instead of improving visualization of subsurface, non-oncogenic turbid tissues. Moderate mechanical compression has been used to increase local cellular concentration to enhance light absorption and reduce light scattering in order to improve the contrast between bone/teeth structure and skin (U.S. Pat. No. 5,429,120); however, this technique has very limited ability to improve the visualization of soft or turbid tissues and their structure.

None of these techniques provide the desired visualization of tissues which are normally turbid for diagnosis and treatment. Alternative techniques are needed to improve visualization for the diagnosis and monitoring of a variety of injuries and diseases and to enhance certain laser treatments and therapies. In addition, imaging modalities, such as optical coherence tomography (OCT) and confocal imaging, that are used for the diagnosis of pathological sites would benefit from an increased imaging distance.

SUMMARY OF THE INVENTION

The present invention provides new and effective methods of reducing light attenuation in biological media or tissue that include index matching the cellular components of the biological media such that the amount of light reflection and refraction by the tissue is reduced or the use of agents that reduce absorption of light. Thus light penetration of the biological media is enhanced and visualization of underlying tissues is improved.

As used in this specification and the appended claims and in accordance with long-standing patent law practice, the singular forms "a" "an" and "the" generally mean "at least one", "one or more", and other plural references unless the context clearly dictates otherwise. Thus, for example, references to "a tissue", "a medium" and "a method" include mixtures of tissues, one or more media and a plurality of methods of the type described; and reference to "a tissue" includes different species of such tissue, for example, muscle, neural and connective tissues, and so forth.

Biological media or tissue is normally turbid, that is, the random reflection and refraction of light by tissue reduces the penetration of the light into the tissue and reduces the visualization of tissues beneath the exterior surface. Light penetration is further decreased by absorption in the tissue. Herein, "biological media or tissue" is defined as including tissue from a plant, animal or person as well as tissue phantoms and other artificial tissues, such as artificial skin, created by the hand of man.

In one aspect the invention comprises a method of index matching the biological media by replacing inter and/or intrastitial (extracellular) fluid with another (replacement) fluid that has a refractive index more similar to that of the inter/intra cellular components of the biological media than water or the tissue fluid.

Herein, "light attenuation" is defined as reducing light scattering and/or light absorption. "Index matching" is defined as altering the ratio of the inter- and intracellular refractive indices of one or more tissue constituents to light such that the ratio more closely approximates one (1) than the native state. "Light" is defined as electromagnetic radiation which comprises wavelengths from about 4000 angstroms (extreme violet) to about 7700 angstroms (extreme red). Such electromagnetic radiation may also be referred to as light radiation or visible radiation and comprise any wavelength within this range. Thus in certain cases, electromagnetic radiation also refers to infrared (IR) and ultraviolet (UV) radiation. "Absorption" is defined as the energy of light radiation that is transferred to a medium through which the light radiation is passing.

In one embodiment of the invention the replacement fluid has a lower absorption coefficient than water.

In another embodiment the replacement fluid comprises glycerol, a dextrose solution or a perfluorocarbon.

In one aspect of the invention the density of the biological tissue is increased.

In another aspect of the invention the water content of the tissue is decreased.

In yet another aspect of the invention the average index of refraction of the tissue is increased.

In yet a further embodiment the reduction in light reflection and refraction is reversible.

The invention further provides a method of enhancing the visualization of turbid biological tissue comprising the reduction of light reflection and refraction. In one illustrative system of the invention the amount of light reflection and refraction in the biological tissue is reduced by about one order of magnitude for visible wavelengths of light.

In another aspect the invention comprises a method of altering light absorption by tissue.

In yet another embodiment the invention provides a method of reducing light scattering in biological media comprising isolating turbid biological media and delivering a replacement fluid that has a refractive index closer to that of the inter/intracellular components of the media than to that of the tissue fluid of the biological media.

In one illustrative system, the replacement fluid is delivered to soft, turbid tissue.

In a further embodiment of the invention, the replacement fluid is replaced by another biocompatible fluid such that the refractive index in the biological tissue is allowed to approximate, or even return to, a native or normal physiological state. In one embodiment this biocompatible fluid comprises saline.

The turbid tissue may comprise one or more tissues including, but not limited to, skin, dermis, mucous membranes, neural tissues, muscle, connective tissues and internal organs. More specifically, these tissues may include, but are not limited to, respiratory tissue, for example gills or lungs, tissues and organs which comprise the digestive, reproductive and excretory systems, for example the esophagus, stomach, intestines, gonads, vagina, mammary glands, seminal vesicles, ureter, and urethra. In addition, turbid tissue includes the organs and tissues that comprise the central nervous system, for example the brain and spinal cord, and the peripheral nervous system.

In a further aspect of the invention the delivery of the replacement fluid comprises injection of the fluid into dermis or removal of a portion of the epidermis layer by the use of a chemical peel, mechanical debridement or ablation, for example by a laser. In an illustrative system, injection of the fluid comprises the use of a hypodermic needle or a high velocity jet.

In another aspect, the delivery of the replacement fluid comprises a topical application. Topical application can include the use of a chemical peel, mechanical debridement or ablation.

In yet another embodiment the invention provides a method of increasing the light penetration of turbid biological tissue comprising the reduction of light reflection and refraction and the alteration of tissue light absorption properties.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1.

FIG. 2.

FIG. 3. Optical properties for native skin, after 1 and 10 minutes soaking in glycerol, and 1 and 10 minutes after PBS rehydration. "t" is the thickness of the tissue sample.

FIG. 4. Optical properties for native skin, after 1 and 10 minutes soaking in dextrose, and 1 and 10 minutes after PBS rehydration. "t" is the thickness of the tissue sample.

FIG. 5.

FIG. 6. In vivo hamster skin after subdermal injection of anhydrous glycerol.

FIG. 7. OCT cross section images of hamster skin overlying human hair.

DESCRIPTION OF ILLUSTRATIVE EMBODIMENTS

A novel technique has been developed to reduce light scattering and/or light absorption at visible and infrared wavelengths in turbid biological media. An important advantage of this technique is that a transient window is established to enhance light transmission through tissues which are normally turbid. Biocompatible fluids with refractive indices closer to that of bulk tissue are added to the tissue to induce an index matching phenomenon. This technique allows enhanced light penetration which, for example, is useful for photocoagulation and imaging through turbid biological substances.

The technique described herein works by reducing the light scattering in tissue unlike current technology which increases light scattering. The amount of light scattering is reduced by index matching the cellular components. As a result more light gets through the normally turbid tissue. Moreover, this process is reversible when the index matching fluid is displaced by saline or another appropriate physiologically compatible solution. Thus, a transient state is established which can be used to perform imaging and/or treatment of living tissue after which the tissue is allowed to return to its normal state.

The invention also provides methods of reducing the absorption of light by tissue. Materials that reduce light absorption have an absorption coefficient that is less than the absorption coefficient of water at selected wavelengths between 0.9 and 20 microns. Of course, the skilled artisan will understand that any wavelength within the continuous range 0.9–20 microns can be used. For example,.0.9000, 0.90001, 0.90002, etc.; 0.9100, 0.9101, 0.9012, etc.; 0.9500, 0.9501, 0.9502, etc.; 1.0000, 1.0001, 1.0002, etc.; 2.0000, 2.0001, 2.0002, etc.; 3.0000, 3.0001, 3.0002, etc.; 4.0000, 4.0001, 4.0002, etc.; 5.0000, 5.0001, 5.0002, etc.; 6.0000, 6.0001, 6.0002, etc.; 7.0000, 7.0001, 7.0002, etc.; 8.0000, 8.0001, 8.0002, etc.; 9.0000, 9.0001, 9.0002, etc.; 10.0000, 10.0001, 10.0002, etc.; 11.0000, 11.0001, 11.0002, etc.; 12.0000, 12.0001, 12.0002, etc.; 13.0000, 13.0001, 13.0002, etc.; 14.0000, 14.0001, 14.0002, etc.; 15.0000, 15.0001, 15.0002, etc.; 16.0000, 16.0001, 16.0002, etc.; 17.0000, 17.0001, 17.0002, etc.; 18.0000, 18.0001, 18.0002, etc.; 19.0000, 19.0001, 19.0002, etc.; 20.9999.

In certain instances, it is desirable that the refraction index of an index-matching agent be less than 1.65 with respect to water (wherein the refraction index of water is about 1.33) and may be desirable for the refraction refraction index of the index-matching agent be about 1.4, again with respect to water. Of course, the skilled artisan will recognize that an index-matching agent with a refraction index as high as 1.75 or as low as 1.35 can be usefull in the present invention.

The skilled artisan will also understand that any agent with a refractive index within the continuous range of 1.35–1.75 can be useful in the invention. It will be understood that by "continuous range of 1.35–1.75" is meant inclusion of all values within this range including, for example, 1.3501, 1.3502, 1.3503, etc.; 1.3601, 1.3602, 1.3603, etc.; 1.3701, 1.3702, 1.3703, etc.; 1.3801, 1.3802, 1.3803, etc.; 1.3901, 1.3902, 1.3903, etc.; 1.4000, 1.4001, 1.4002, etc.; 1.4101, 1.4102, 1.4103, etc.; 1.4200, 1.4201, 1.4202, etc.; 1.4300, 1.4301, 1.4302, etc.; 1.4400, 1.4401, 1.4402, etc.; 1.5000, 1.5001, 1.5002, etc.; 1.5500, 1.5501, 1.5502, etc.; 1.6000, 1.6001, 1.6002, etc.; 1.6500, 1.6501, 1.6502, etc.; 1.6601, 1.6602, 1.6603, etc.; 1.6701, 1.6702, 1.6703, etc.; 1.6801, 1.6802, 1.6803, etc.; 1.6901, 1.6902, 1.6903, etc.; 1.7000, 1.7001, 1.7002, etc.; 1.7400, 1.7401, 1.702. etc.

The studies presented illustrate the effects that an index-matching agent has on the optical properties of skin. While a number of agents may be used, such as glucose solution, dextrose solution or Trazograph (a 2-4-6 triiodo-benzene acid preparation), glycerol is the exemplary agent used in many of the described examples. Glycerol is a biologically inert, hyperosmotic agent that is widely used in cosmetics and medicine. In addition, it has a refractive index of about 1.47 (Gregory, 1991), which is similar to that of major skin tissue constituents, such as collagen (refractive index of about 1.53) (Wang et al., 1996).

The mechanism by which glycerol causes an increase in light transmission through tissue is hypothesized to be a combination of index matching and dehydration. Tissue consists of many constituents that have a similar refractive index that is quite different from that of the water making up the intercellular space. A hyperosmotic index-matching agent can be used to replace much of the intercellular water temporarily, creating a more uniform index-matched environment within the tissue. More light is transmitted because of the decreased scattering in addition to the thinning of the sample caused by dehydration. Light at infrared wavelengths which is highly absorbed by water may be less attenuated due to a decrease in the water content.

The inventors hypothesized that light transmission through the skin increases because glycerol acts as both a dehydrating and an index-matching agent. The hyperosmotic nature of glycerol draws interstitial water out of the tissue, and if the tissue is exposed to a significant amount of glycerol, it may replace some of the water. Dehydration of the tissue reduces the amount of refractive index mismatch, because the mismatch due to the water has been omitted. In addition, if parts of the interstitial space are temporarily filled with the index matching agent, the random scattering that is normally seen due to the water-cellular component index mismatch is reduced. While dehydration that decreases tissue thickness leads to an increase in light transmission, there is also an overall decrease in the reduced scattering coefficient and absorption coefficient of the tissue.

The potential of the method towards imaging was shown for the specific case of OCT. OCT is a relatively new imaging modality which measures light reflection from a volume of tissue (Huang et al., 1991; Izatt et al., 1993; Schmitt, et al., 1994). Excised hamster skin with dark brown human hair placed underneath was imaged with OCT before and after the application of glycerol. The results demonstrate that the glycerol reduced excessive scattering in the tissue enough to image an underlying area which was previously not visible.

The inventors found it preferable in the examples described herein to apply glycerol to the dermal side of all skin samples, since the penetration of glycerol through the epidermis is quite limited due to the protective nature of the stratum corneum. By doing so, an increase in the transmittance of light was seen almost immediately after application of glycerol to the dermal side of both in vitro and in vivo samples. Within the 20 minutes the reduced scattering coefficient was decreased by as much as fivefold in the visible region of the spectrum. The effect was quickly and easily reversed by rinsing out the tissue with physiologic saline solution.

Although glycerol is an exemplary agent, the skilled artisan will understand that other index matching agents can be used. The index matching fluid is preferably biocompatible. Until the fluid diffuses or is metabolized, a transient reduction in light scattering is established which allows more photons to be transmitted into and out of the tissue. As a result, it is easier to image into tissues and/or deliver light into tissues for treatment. Comparing the in vivo and in vitro images provided in the examples described herein indicate that the optical property changes produced in vitro and in vivo are similar. Thus other index matching agents which are shown to produce the desired optical property changes in vitro as presented herein can also be useful in the invention.

Since epidermis protects the skin and body from foreign substances, a variety of methods for delivery of index matching fluid to the dermis may be used. In some cases, it may be easier to selectively remove a portion of the epidermal layer. This can be achieved by using a $CO_2$ or a Er:YAG laser which are used for laser skin resurfacing. However, other means well-known to skilled artisans, such as using chemical peels, ablation, or mechanical debridement can remove the epidermal layer for the delivery of the index matching fluids. On the other hand, the fluids can be injected into the dermis by a fine hypodermic needle or by a high velocity jet.

In order to optimize the method while applying an index-matching agent topically, a method that increases the delivery of the agent to the dermis is preferred. Some possibilities lie in removal of the epidermis by laser resurfacing a small area, or by a transdermal drug delivery device; however, the skilled artisan will be aware that certain methods will be preferred in some circumstances.

Because the technique is temporary and reversible in addition to being minimally invasive, it should be quite useful in therapeutic and diagnostic techniques which benefit from an increase in light transmission. For example, in dermatology, treatment of Port Wine Stains (PWS) and spider veins can benefit from this technique. PWS involves the abnormal over-growth of dermal vasculature in the dermis. Spider veins are superfluous veins in the extremities, typically buried 1 mm beneath the skin surface. Laser light has been used to coagulate the over-grown vasculature and the superfluous veins (Tan, 1992). When new vasculature is regenerated to replace the coagulated vessels, the amount of the abnormal blood vessels is reduced. This technique can enhance laser treatments by reducing light scattering in the dermis. As a result, more laser light penetrates into the target vessels, minimizing unnecessary thermal damage to the surrounding dermis.

In addition, photodynamic therapy (PDT) can be enhanced by this technique. Cancerous cells selectively accumulate a photo-sensitive drug which is photoactivated by laser light. One of the major obstacles in the widespread application of PDT is delivering sufficient light to a buried tumor (Welch and van Gemert, 1995). Reducing the light attenuation of tissue, such as the dermis, increases light transmission so that more light penetration into the tumor to activate the PDT drugs.

Interstitial photocoagulation can also benefit from this technique. Coagulated tissue generally has a higher scattering coefficient than native tissue. When index matching fluid is used to reduce light scattering in coagulated tissue, increased light penetration is achieved. As a result, deeper interstitial photocoagulation can be obtained with this index-matching process.

Figure 3A:
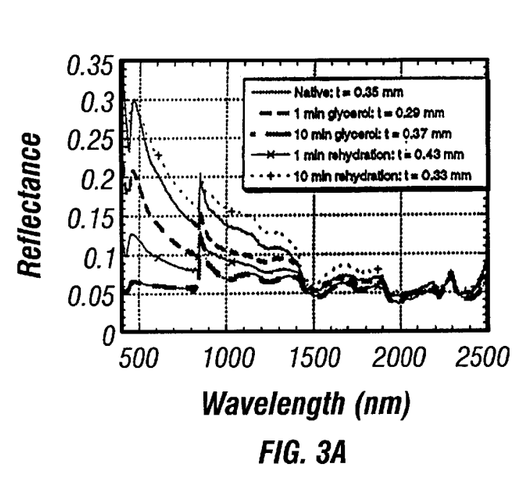
(FIG. 3A) Rat skin diffuse reflectance.
Figure 3B:
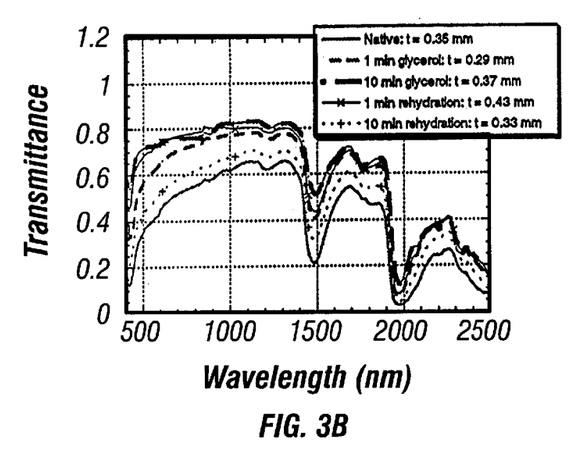
(FIG. 3B) Rat skin transmittance.
Figure 3C:
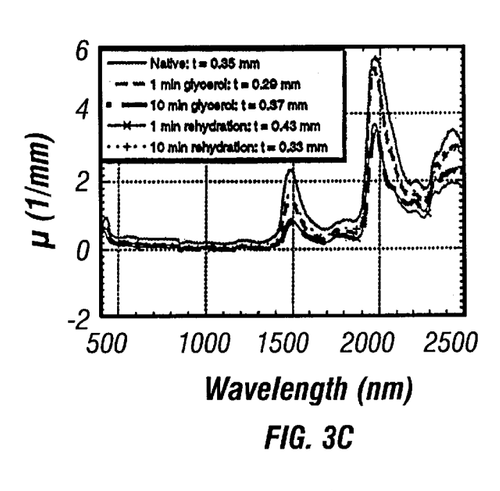
(FIG. 3C) Rat skin absorption coefficient.
Figure 3D:
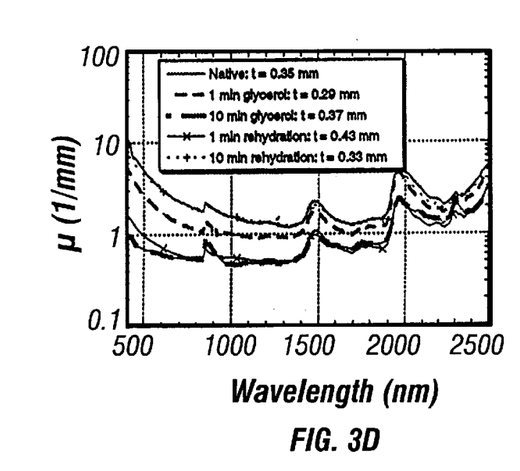
(FIG. 3D) Rat skin reduced scattering coefficient.
Figure 4A:
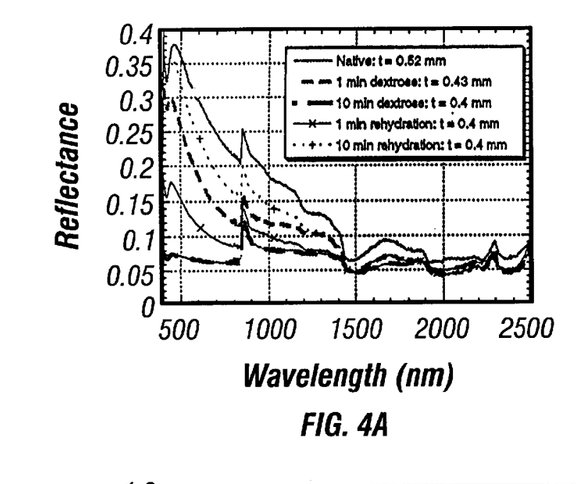
(FIG. 4A) Rat skin diffuse reflectance.
Figure 4B:
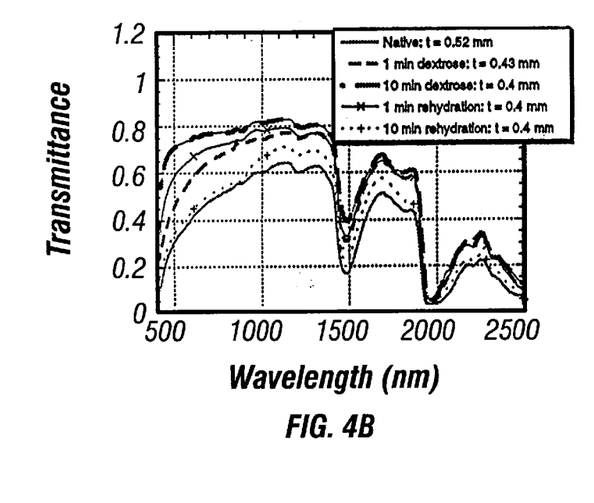
(FIG. 4B) Rat skin transmittance.
Figure 4C:
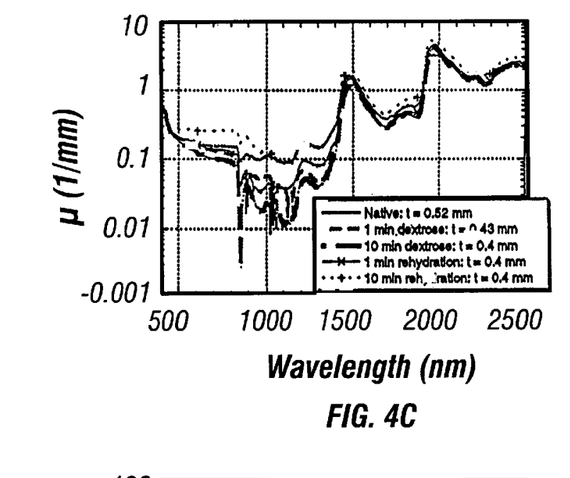
(FIG. 4C) Rat skin absorption coefficient.
Figure 4D:
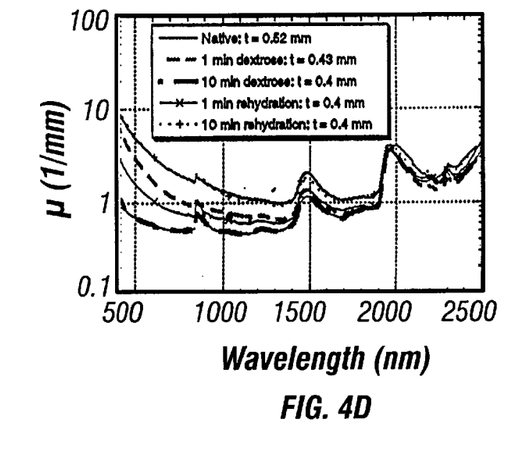
(FIG. 4D) Rat skin reduced scattering coefficient.

Furthermore, it is conceivable to use a water miscible fluid to alter light absorption properties of soft tissues. Optical property measurements have demonstrated that tissue water concentration changes by adding an index matching fluid, as illustrated by the changes in the local water absorption peaks at 1450 and 1930 nm (FIG. 3C and FIG. 4C). Depending on the reduction of water concentration, soft tissue optical properties about the water absorption peaks could be controlled by the introduction of a miscible fluid. This absorption reduction technique can be used to modify light penetration depth of tissue for lasers about a water absorption peak.

Another therapeutic application is hair removal. In this procedure, light is used to damage the hair follicles, causing temporary or permanent hair loss. Reduction in the light scattering of skin can allow more light to penetrate to the hair follicle, causing more complete follicle destruction with less damage to other parts of the skin.

The technique disclosed herein can also be used in diagnostic applications such as providing better visualization of the vasculature which can allow better planning of laser treatment parameters.

Another dermatological diagnostic application is to enhance visualization of abnormal growth of moles. Melanoma is one of the most common cancers in the United States. Early detection of abnormal mole growth is said to be one of the best ways to combat this cancer. Besides performing a biopsy, the current clinical technique superficially detects mole size and shape. Reduction of scattering in skin can allow better visualization of moles within the dermis, providing more information to determine the pathology of the mole.

For oncology, minimal invasive diagnostic techniques such as fluorescence spectroscopy identification of buried pre-cancerous/cancerous cells can also be augmented. The reduction of scattering allows excitation light to penetrate deeper in tissue and improve the signal to noise ratio of detected fluorescence and reduce the filtering effect of scattering upon the remitted fluorescence.

Possibly the greatest number of beneficiaries of this technique are diabetics who must daily monitor their blood glucose level. For example, a closed loop system that monitors glucose level constantly can be developed by incorporating this index matching technique. Reduction of scattering allows more light to be delivered into tissue for detecting glucose level. As a result, more signal can be detected for a more accurate measure of glucose concentration.

The invention provides a novel technique which improves the imaging of tissues. The reduction in scattering can improve the depth of penetration and increases signal to noise values in techniques such as optical coherence tomography (OCT), confocal microscopy, time- and frequency-domain photon migration. These techniques allow non-invasive determination of tissue structure and function, and are valuable for in vivo, in vitro, and forensic analysis. The local increase in index of refraction and density of the affect tissue can increase the contrast of the tissue in optical or ultrasonic images.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

In Vitro Index Matching in Rat Skin and Visualization of Turbid Tissue

Methods:

To demonstrate this technique, in vitro index matching experiments were performed on skin specimens. Glycerol and a dextrose solution (a form of glucose solution) were used as index matching fluids. The concentration of the dextrose solution was 1.4 g/mL. Both of these fluids are biocompatible with extremely high lethal dosage. The refractive index of glycerol is 1.47 (Gregory, 1991) and that of dextrose solution is approximately 1.44 (Weast, ed., 1986). Since skin tissue is rich in type I collagen which has an index of approximately 1.53 (Wang et al., 1996). For dried collagen, the index matching agents match collagen better than water (n=1.33).

Two skin specimens were harvested from a Wistar rat. The sub-dermal muscle layer was removed to expose the dermal collagen (Dimitrov and Bass, 1995). Skin specimens were submerged in either glycerol or a dextrose solution. The optical behavior of each specimen was examined at five different stages: 1) native, 2) soaked in index matching fluid for 1 minute, 3) soaked in index matching fluid for 10 minutes, 4) rehydrated in saline for 1 minute and 5) rehydrated in saline for 10 minutes. At each stage, photographs illustrated the changes of specimen optical properties. Furthermore, reflectance and transmittance of the skin specimen at each stage were measured using a spectrophotometer equipped with an integrating sphere (Pickering et al., 1993). The optical properties (absorption and reduced scattering coefficients) were calculated from the reflectance and transmittance measurements using the Inverse Adding Doubling Model (Prahl, 1995a).

Results

Figure 1A:
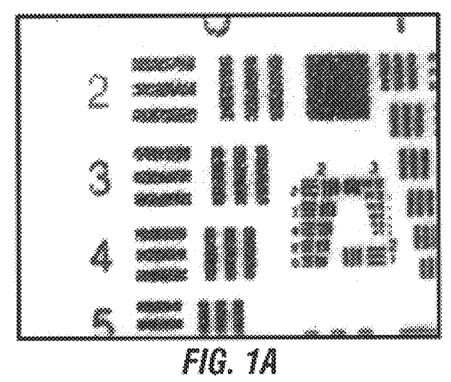
(FIG. 1A) United States Air Force (USAF) resolution target. Original magnification about 7.5×.
Figure 1B:
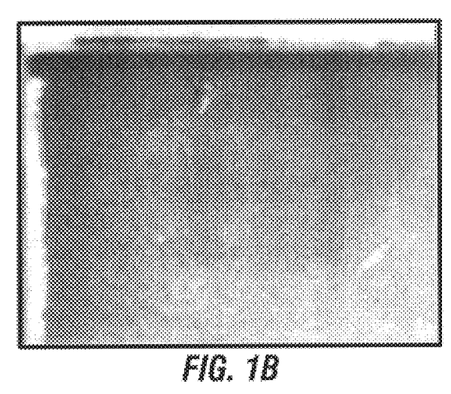
(FIG. 1B) Native rat skin on the USAF resolution target. Original magnification about 7.5×.
Figure 1C:
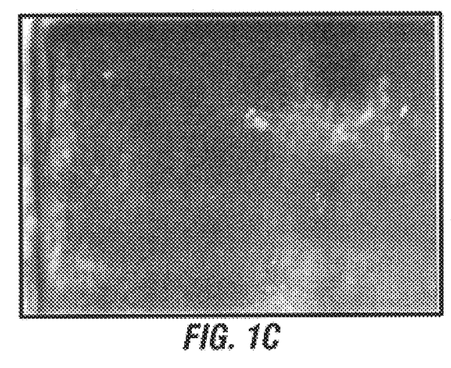
(FIG. 1C) Rat skin after soaking in glycerol for 1 min. Original magnification about 7.5×.
Figure 1D:
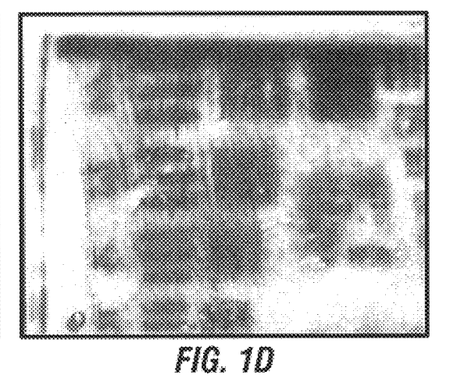
(FIG. 1D) Rat skin after soaking in glycerol for 10 min. Original magnification about 7.5×.
Figure 1E:
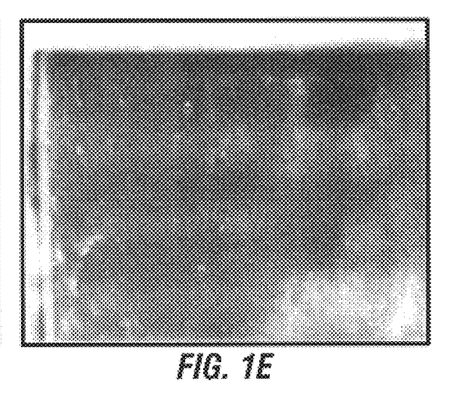
(FIG. 1E) Rat skin after rehydrating in saline for 1 min. Original magnification about 7.5×.
Figure 1F:
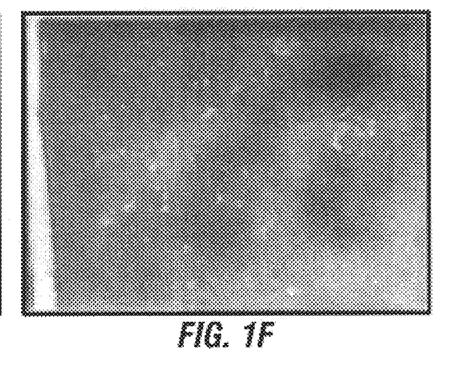
(FIG. 1F) Rat skin after rehydrating in saline for 10 min. Original magnification about 7.5×.
Figure 2A:
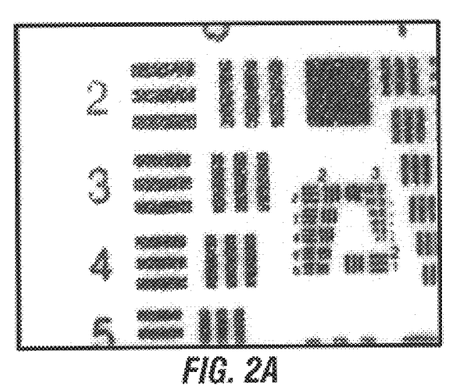
(FIG. 2A) USAF resolution target. Original magnification about 7.5×.
Figure 2B:
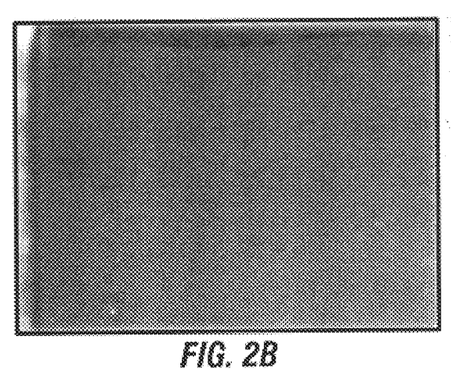
(FIG. 2B) Native rat skin on the USAF resolution target. Original magnification about 7.5×.
Figure 2C:
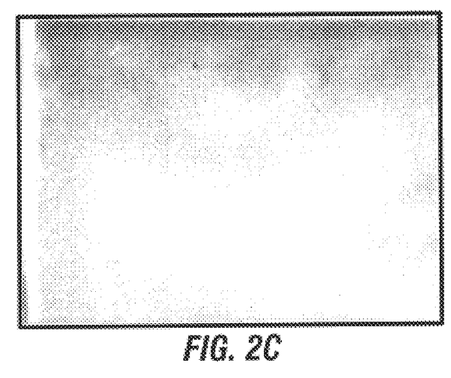
(FIG. 2C) Rat skin after soaking in dextrose solution for 1 min. Original magnification about 7.5×.
Figure 2D:
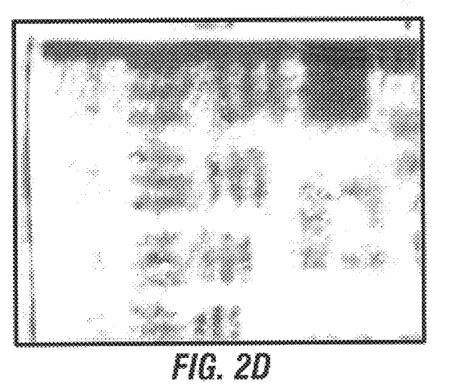
(FIG. 2D) Rat skin after soaking in dextrose solution for 10 min. Original magnification about 7.5×.
Figure 2E:
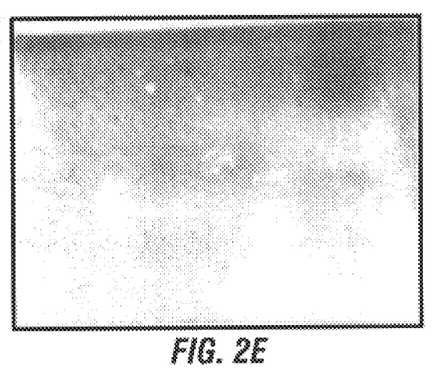
(FIG. 2E) Rat skin after rehydrating in saline for 1 min. Original magnification about 7.5×.
Figure 2F:
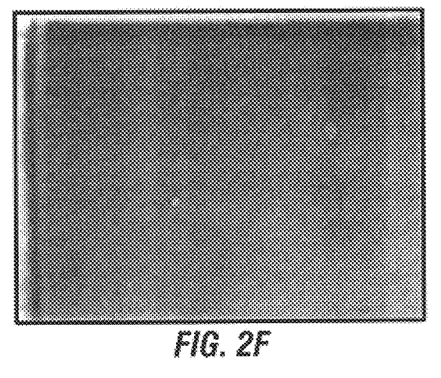
(FIG. 2F) Rat skin after rehydrating in saline for 10 min. Original magnification about 7.5×.

Pictures of the skin specimens taken at each stage in glycerol and in dextrose solution are shown in FIGS. 1A–1F and FIGS. 2A–2F, respectively. A United States Air Force (USAF) resolution target (FIGS. 1A and 2A) was placed under the skin specimen. As the transmittance of light increased through the skin sample because of the index matching agent, better visualization of the resolution target background was obtained as illustrated in FIGS. 1D and 2D. The native skin specimen thicknesses were 0.35 mm for the glycerol specimen and 0.52 mm for the dextrose solution specimen. The measured and calculated optical properties of the skin specimen in glycerol are shown in FIGS. 3A–3D, and those from specimen in dextrose solution are in FIGS. 4A–4D. In using both index matching fluids, an order of magnitude decrease in the reduced scattering coefficient was observed. From the changes in the tissue water absorption peaks, variation of tissue water concentration was approximated from changes in absorption at the water absorption peak at 1450 nm and at 1930 nm. After one minute of soaking in glycerol, the local water absorption peak at 1.45 mm was 58% of that of native tissue. With ten minutes of glycerol soaking, the absorption peak went down to 38%.

This study demonstrated the ability of this technique to provide a transient enhancement of light transmission through skin. Similar in vitro studies were performed on bovine aorta and an increase in light transmission was also observed.

EXAMPLE 2

In Vivo Index Matching in Rat Skin and Visualization of Turbid Tissue

Methods:

In vivo studies were performed on rat skin and visualization protocols as described in Example 1 were again utilized with the following modifications. In this case, topical application of glycerol onto skin did not result in any significant change in tissue optical properties. The epidermis acted as a barrier preventing the penetration of glycerol into the dermis.

Figure 5A:
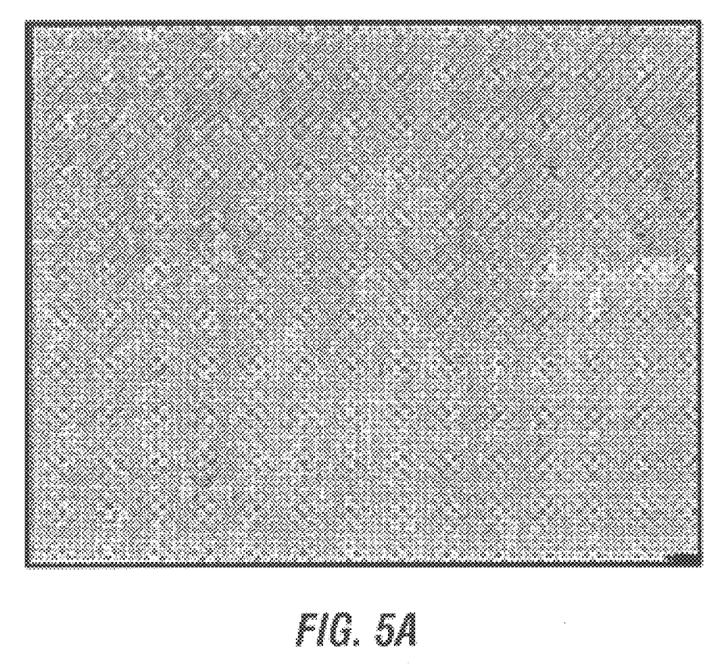
(FIG. 5A) Native rat skin in vivo. Original magnification about 100×.
Figure 5B:
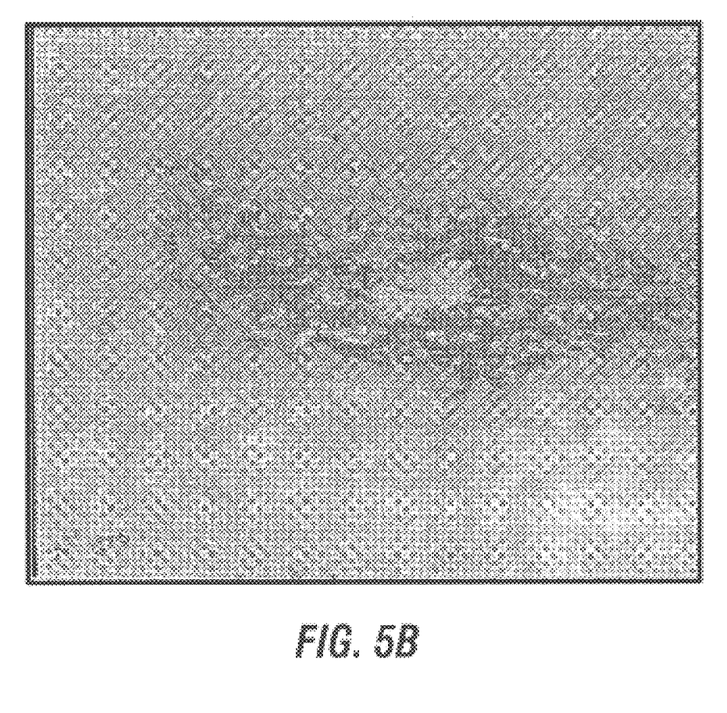
(FIG. 5B) Rat skin in vivo with glycerol injection. The bright spot at the center is the needle tip used for the injection within the skin. Original magnification about 100×.

Results:

Glycerol was injected into rat skin dermis with a hypodermic needle. FIG. 5A shows the skin surface of a Wistar rat before injection; FIG. 5B illustrates the changes in dermal optical properties after glycerol was injected into the dermis. A marked improvement in visualization of the skin tissue was observed. The rat was allowed to survive and no noticeable mark by the needle or the glycerol was observed after 24 hours.

EXAMPLE 3

Decreased Scattering and Increased Visibility Through In Vitro Rat Skin and In Vivo Hamster Skin Methods:

For all trials, animals were anesthetized with a 3:4 mixture of Rompun to Ketamin and given 0.1 ml/kg body weight.

Photographs demonstrating the effect of anhydrous glycerol on in vivo hamster skin were taken. A 1.5 cm long incision was made into the skin on the shaved dorsal area of the hamster and the connective tissue bluntly dissected. A 1 cm×1 cm resolution target with 0.5 mm wide bars was slipped underneath the skin. The glycerol was injected into the area between the target and the skin. Excess glycerol was dabbed off with gauze prior to taking each picture.

Figure 6A:
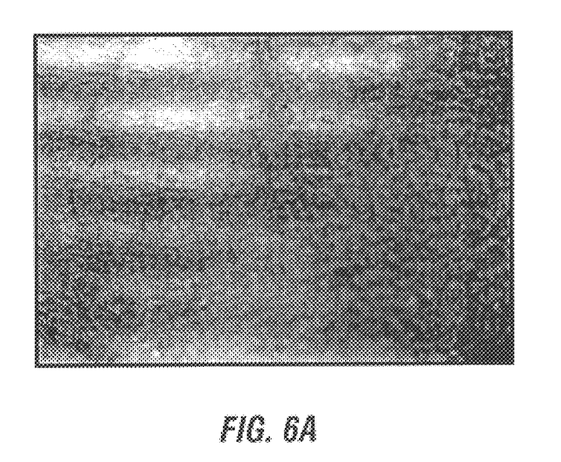
(FIG. 6A) Resolution target (scale bar= 0.5 mm) placed subdermally into native skin.
Figure 6B:
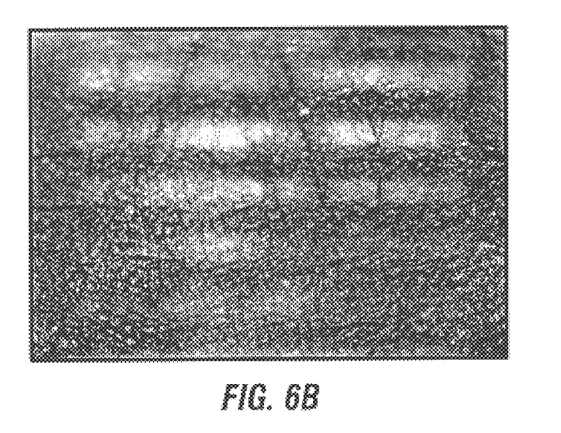
(FIG. 6B) 20 minutes after glycerol application (note the increased visibility of the resolution target as well as the blood vessels in the skin).
Figure 6C:
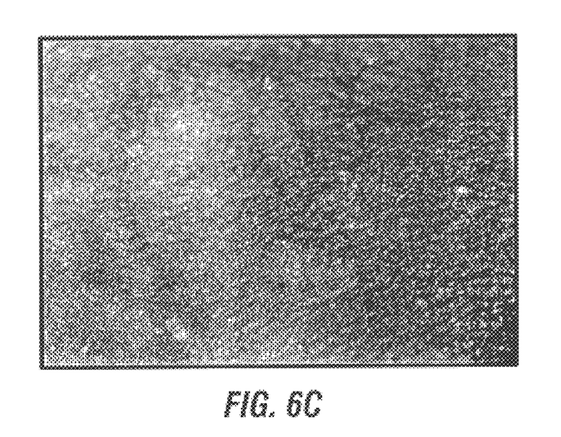
(FIG. 6C) Replacement of glycerol in the skin with PBS for 25 minutes.

Results:

Images taken of in vivo hamster skin exposed to glycerol are shown in FIG. 6. The effect is similar to that seen in excised skin. Initially, the skin is turbid and the bars of the resolution target are not clearly visible. After glycerol is applied, the skin becomes much less scattering and the bars are more visible. In addition, blood vessels which were not clearly seen before are more apparent (note the large diagonal vessel which was not clearly visible in the native tissue). Over-rehydration of the skin by replacement of glycerol by PBS solution makes the skin more turbid than the native tissue. The native skin was slightly dehydrated compared to having been soaked in PBS for 25 minutes.

EXAMPLE 4

Improved Visibility of Structures in Optical Coherence Tomography Images (OCT)

Methods:

The effect of glycerol on hamster skin was also investigated with the use of optical coherence tomography (OCT). OCT images were acquired of a dark brown human scalp hair (75 $\mu$m) placed underneath newly excised hamster skin. The skin was then soaked in glycerol for 10 minutes and replaced on top of the hair for the acquisition of more images.

Figure 7A:
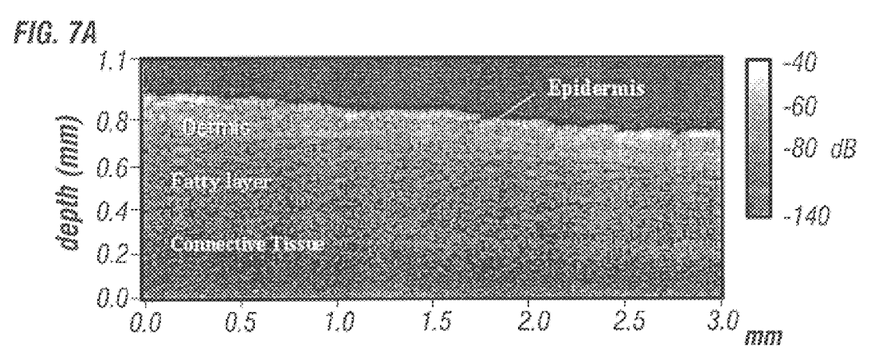
(FIG. 7A) The hair is not visible due to excess scattering in the skin.
Figure 7B:
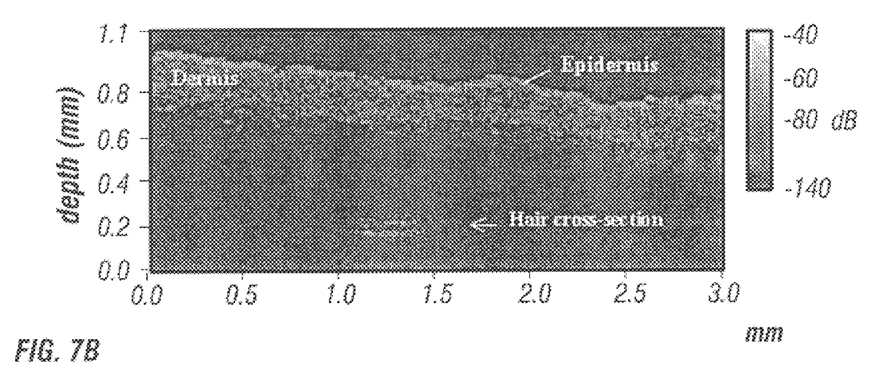
(FIG. 7B) The hair is visible (bright region in lower center) after the hamster skin was soaked in glycerol. The skin appears much darker due to a reduction in scattering.

Results:

The OCT scan of native hamster skin overlain on human hair is shown in FIG. 7A. One can identify the layers in the skin (epidermis, dermis, fat, and collagenous subdermal connective tissue). The underlying hair and tissue border are not seen because the signal drops off too quickly due to the high scattering environment. The changes in the OCT scan after the skin was soaked for 10 minutes in glycerol are shown in FIG. 7B. The skin has much less scattering as can be seen by the larger amount of dark areas. In addition, the underlying hair is now visible (bright region in lower center of image).

EXAMPLE 5

Imaging Turbid Tissues in Humans

The methods described in the above examples can be applied to human tissues. The preferred method for applying the index matching fluid to tissue, and consequently the dosage used, depends on the purpose of imaging the tissue and the application method. In general, the largest injectible dosage is equivalent to replacement of one-half of the tissue water. For topical applications, a maximum dosage is not critical since the unused portion will just remain on the surface.

The lowest useful dosages are also dependent upon the type of tissue being treated. For example, the lowest useful dosage of index matching fluid can be applied topically at a dose of about 0.01–0.2 ml/cm$^2$ affected skin. For mucous membranes, neural tissue, internal organs, muscle, and connective tissue the lowest useful topical application is at a dose of about 0.01–0.2 ml/cm$^2$ affected tissue. For interstitial coagulation of tissue, injection with a needle and syringe is preferred. Injection points approximately every 5 mm of treated tissue are suggested. A minimal injection dosage of 0.01–0.35 ml/cm$^2$ affected tissue is recommended.

Of course, those of skill in the art will recognize that doses between the lowest useful dosage and the maximum dosage will also be useful in the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

DeCoste, S. D., W. Farinelli, T. Flotte and R. R. Anderson. "Dye enhanced laser welding for skin closure." *Lasers in Surgery and Medicine*. 12:25–32. 1992.

Dimitrov, D. and L. Bass. Technical discussion with EC. 1995.

Gregory, S. R., "Physical properties of glycerine," In: Jungermann, E., Sonntag, N. O. V., Eds., Glycerine: A Key Cosmetic Ingredient. New York: Marcel Cekker, Inc. 1991. pp. 113–156.

Hiramoto, Y. "Refractive index of the protoplasm in sea urchin eggs." *Development, Growth, and Differentiation*. 1(2):141–148. 1979.

Huang, H. D., Swanson, E. A., Lin, C. P., Schuman, J. S., Sinson, W. G., Chang, W., Hee, M. R., Flotte, T., Gregory, K., Puliafito, C. A., Fujimoto, J. G., "Optical coherence tomography," *Science*, 254:1178–1181, 1991.

Izatt, J. A., Hee, M. R., Huang, C., Swanson, E. A., Lin, C. P., Schuman, J. S., Puliafito, C. A., Fujimoto, J. G., "Micron-resolution biomedical imaging with optical coherence tomography; *Opt. Photon News*, 4:14–19; 1993.

Jungermann E. and N. O. V. Sonntag. "Glycerine: A key cosmetic ingredient." New York, N.Y. Dekker. 1991.

Pickering, J. W., S. A. Prahl, N. van Wieringen, J. F. Beek, H. J. C. M. Sterenborg, and M. J. C. van Gemert. "Double-integrating sphere system for measuring the optical properties of tissue." *Applied Optics*. 32(4): 399–558, 1993.

Schmitt, J. M., Knuttel, A., Eckhaus, M. A., "Optical-coherence tomography of a dense tissue: Statistics of attenuation and backscattering," *Phys. Med Biol.*, 29:1704, 1994.

Prahl, S. "Optical property measurements using the Inverse Adding-Doubling program." A computer software for the PCs. March, 1995a.

Prahl, S. A., "The Adding-Doubling Method," In: Welch A. J., van Gemert M. J. C., eds. OPTICAL-THERMAL RESPONSE OF LASER-IRRADIATED TISSUE, New York: Plenum Press, 101–125, 1995b.

Tan, O. T. *Management and treatment of benign cutaneous vascular lesions*. Philadelphia, Pa., Lea & Febiger. 1992.

Vitkin, I., J. Woolsey, B. Wilson and R. R. Anderson. "Optical and thermal characterization of natural melanin." *Photochemistry and Photobiology*. 59:455–462. 1994.

Wang, X., T. E. Milner, M. C. Chang and J. S. Nelson. "Group refractive index measurement of dry and hydrated type I collagen films using optical low-coherence reflectometry." *Journal of Biomedical Optics*. 1(2):212–216. 1996.

Weast, R. C. ed. *CRC Handbook of chemistry and physics*. Boca Raton. Fla., CRC Press, Inc. 1986.

Welch, A. J. and Gemert, M. J. C. *Optical-thermal response of laser-irradiated tissue*. New York, N.Y., Plenum Press, 1995.

What is claimed is:

1. A method of reducing light attenuation within biological media, comprising:
    delivering an effective amount of biocompatible fluid within said biological media to:
        soak said biological media with said biocompatible fluid;
        replace intercellular fluid within said biological media with said biocompatible fluid; and
        reduce light reflection and refraction among intercellular and intracellular components within said biological media to enhance light transmission through said media.

2. The method of claim 1, wherein said biological media comprises a turbid media.

3. The method of claim 2, wherein said biological media comprises one or more of the group consisting of skin, dermis, mucous membranes, neural tissue, muscle, connective tissues, respiratory tissue, reproductive tissues, excretory tissues and digestive tissues.

4. The method of claim 3, wherein said biological media comprises skin.

5. The method of claim 1, wherein density of said biological media is increased.

6. The method of claim 1, wherein water content of said biological media is decreased.

7. The method of claim 1, wherein the index of refraction of said biological media is increased.

8. The method of claim 1, wherein said biocompatible fluid comprises glycerol.

9. The method of claim 1, wherein said biocompatible fluid comprises a dextrose solution.

10. The method of claim 1, wherein said biocompatible fluid has a lower absorption coefficient than water.

11. The method of claim 10, wherein said biocompatible fluid comprises perfluorocarbon.

12. The method of claim 1, wherein said light reflection and refraction is reduced by about one order of magnitude for visible wavelengths of light.

13. The method of claim 1, wherein said reduction of light reflection and refraction is reversible.

14. A method of reducing light scattering within biological tissue, said method comprising:

delivering a first biocompatible fluid within said biological tissue;

soaking said biological tissue with said first biocompatible fluid;

replacing intercellular fluid of said biological tissue with said first biocompatible fluid; and reducing light scattering within said biological tissue by causing the ratio of refractive index of cellular components within the tissue to the refractive index of intercellular fluids to be closer to one than a native state.

15. The method of claim 14, wherein said cellular components include cellular fluids.

16. The method of claim 14, wherein said biological tissue comprises a turbid media.

17. The method of claim 14, wherein said biological tissue comprises skin.

18. The method of claim 14, wherein said biocompatible fluid is replaced by a second biocompatible fluid.

19. The method of claim 18, wherein said replacement with the second biocompatible fluid is such that the ratio of refractive index of cellular components within the tissue to the refractive index of intercellular fluids returns to the native state.

20. The method of claim 19, wherein said second biocompatible fluid comprises saline.

21. The method of claim 14, wherein said delivery comprises injection.

22. The method of claim 21, wherein said injection is by a hypodermic needle or a high velocity jet.

23. The method of claim 14, wherein said delivery comprises topical application preceded by removal of at least a portion of epidermis by ablation, chemical peel or mechanical debridement.

24. A method of reducing light attenuation within biological media, said method comprising:

providing a replacement fluid having a lower absorption coefficient than water at one or more water absorption peaks; and delivering an effective amount of said replacement fluid within said biological media to:
soak said biological media with said replacement fluid;
replace intercellular fluid within said biological media with said replacement fluid; and
reduce light absorption within said biological media.

* * * * *